United States Patent [19]

Staniec

[11] Patent Number: 5,462,656
[45] Date of Patent: Oct. 31, 1995

[54] CUTTING OIL TREATMENT APPARATUS

[75] Inventor: Robert Staniec, Playa del Rey, Calif.

[73] Assignee: Harvey Universal, Inc., Torrance, Calif.

[21] Appl. No.: 205,944

[22] Filed: Mar. 1, 1994

Related U.S. Application Data

[62] Division of Ser. No. 42,120, Apr. 2, 1993, Pat. No. 5,314,620.

[51] Int. Cl.⁶ ..................................................... C02F 3/10
[52] U.S. Cl. ........................... 210/150; 210/251; 409/136
[58] Field of Search ..................................... 210/610, 611, 210/631, 764, 150, 151, 209, 220, 251, 194; 409/136

[56] References Cited

U.S. PATENT DOCUMENTS

| | | |
|---|---|---|
| 895,229 | 8/1908 | Beddoes . |
| 3,051,315 | 8/1962 | Boester ............................ 210/195.1 |
| 4,035,289 | 7/1977 | Guillerme et al. ................... 210/611 |
| 4,253,951 | 3/1981 | McCune ............................. 210/631 |
| 4,325,663 | 4/1982 | Lee ..................................... 409/136 |
| 4,584,102 | 4/1986 | Bogart et al. ....................... 210/610 |
| 4,902,432 | 2/1990 | Kuno .................................. 210/764 |
| 4,923,619 | 5/1990 | Legros ................................ 210/764 |

Primary Examiner—Thomas Wyse

[57] ABSTRACT

A method and apparatus for the biological purification of cutting oil, such as used in metal machining apparatus, is disclosed. The invention herein provides a suitable environment for cultured aerobic bacteria. These beneficial bacteria act to break down the hazardous organic waste products of anaerobic bacteria and eliminate rank odors. The cutting oil is aerated to encourage the proliferation of the aerobic bacteria, and to discourage the proliferation of the unwanted anaerobic bacteria.

8 Claims, 3 Drawing Sheets

CUTTING OIL TREATMENT APPARATUS

This is a divisional of application of U.S. Ser. No. 08/042,120, filed Apr. 2, 1993, now U.S. Pat. No. 5,314,620.

TECHNICAL FIELD

This invention relates to methods and materials for cleaning cutting oil used in the machining of metal parts.

BACKGROUND OF THE INVENTION

Cutting oil is a generic term for that class of oils which are used in metal machining operations. Cutting oil generally comprises one or more mineral oil, chlorinated or sulfurized mineral oil, fatty oil, or mixtures thereof. The cutting oil is provided at the cutting surface where a metal-shaping bit is used to modify a metal workpiece. Cutting oil provides a lubricating film between the cutting bit and the workpiece, thus keeping the cutting area cooled. The continuous flow of cutting oil acts to retain metal shards or flakes formed during the cutting process, and to carry these flakes away from the cutting surface. The cutting oil can also contain anti-corrosion agents, emulsifiers, anti-bacterial agents, and the like.

One example of a machining apparatus 110 is shown in FIG. 1. A workpiece 112 (shown in cross section) is supported below a cutting bit 114. The workpiece 112 and the cutting bit 114 are moved relative to one another, either by motion controls such as the handle means 116 shown, or by computer controls (not shown). Generally, motion controls provide relative movement along each of the x, y and z axis.

A reservoir of cutting oil is maintained within the body of the machining apparatus 110. The cutting oil is pumped to a nozzle 118 located proximal to the cutting surface. The cutting oil is sprayed over the workpiece 112 and the cutting bit 114. A drain system (not shown) returns the cutting oil to the reservoir.

The presence of metal flakes in the cutting oil has traditionally limited the effective use life of cutting oils. However, a variety of methods have been developed to enhance the life of the cutting oil by filtering the oil, either before it is sent to the cutting oil reservoir, while it is held within the reservoir, or as it is brought to the cutting surface. Generally, the larger flakes are removed by filtration or straining. The smaller metal flakes can be removed by skimming or other processes. Cutting oil can be filtered by the processes described in U.S. Pat. No. 4,325,663, for example.

Cutting oil can become contaminated by anaerobic bacteria. The presence of anaerobic bacteria in the cutting oil reservoir causes rank and rancid odors, limiting the useful life of the cutting oil for aesthetic reasons. The presence of the anaerobic bacteria can also provide a source of irritation or contagion for the humans who must come into contact with the cutting oil in either liquid or volatilized form.

SUMMARY OF THE INVENTION

A method and apparatus for the biological purification of cutting oil, such as used in metal machining apparatus, is disclosed. The invention herein provides beneficial, aerobic bacteria which act to break down the hazardous organic waste products of anaerobic bacteria. The cutting oil is aerated to encourage the proliferation of the seeded aerobic bacteria, and to discourage the proliferation of unwanted anaerobic bacteria.

Specifically, a method for the biological purification of cutting oil comprises the steps of aerating cutting oil; introducing aerobic nitrifying bacteria into the aerated cutting oil; and supporting the aerobic proliferation of the introduced bacteria.

The aerobic bacteria are preferably introduced in a medium which includes an inorganic base material upon which the cultured aerobic bacteria are supported. Alternatively, an oil-based culture of appropriate bacteria can be introduced into the cutting oil. When an oil-based culture is introduced, the oil base should not interfere with the use of the cutting oil.

The aerobic bacteria are innocuous to humans. Generally, the aerobic bacteria includes at least one of a *nitrobacter sp.* or a *pseudomonas sp.* Aeration is preferably done before the introduction of the bacteria culture, and continued subsequent to the introduction of the culture, to promote the growth of the beneficial bacteria.

In accordance with the invention herein, an improved apparatus for machining metal is also presented. The improved metal machining apparatus includes, within a cutting oil reservoir, an aeration source and a cultured aerobic bacteria source.

BRIEF DESCRIPTION OF THE DRAWINGS

The Figures are drawn for clarity and are not drawn to scale. Similar numbers refer to similar structures throughout the Figures.

DISCLOSURE OF THE INVENTION INCLUDING BEST MODE

Figure 1:
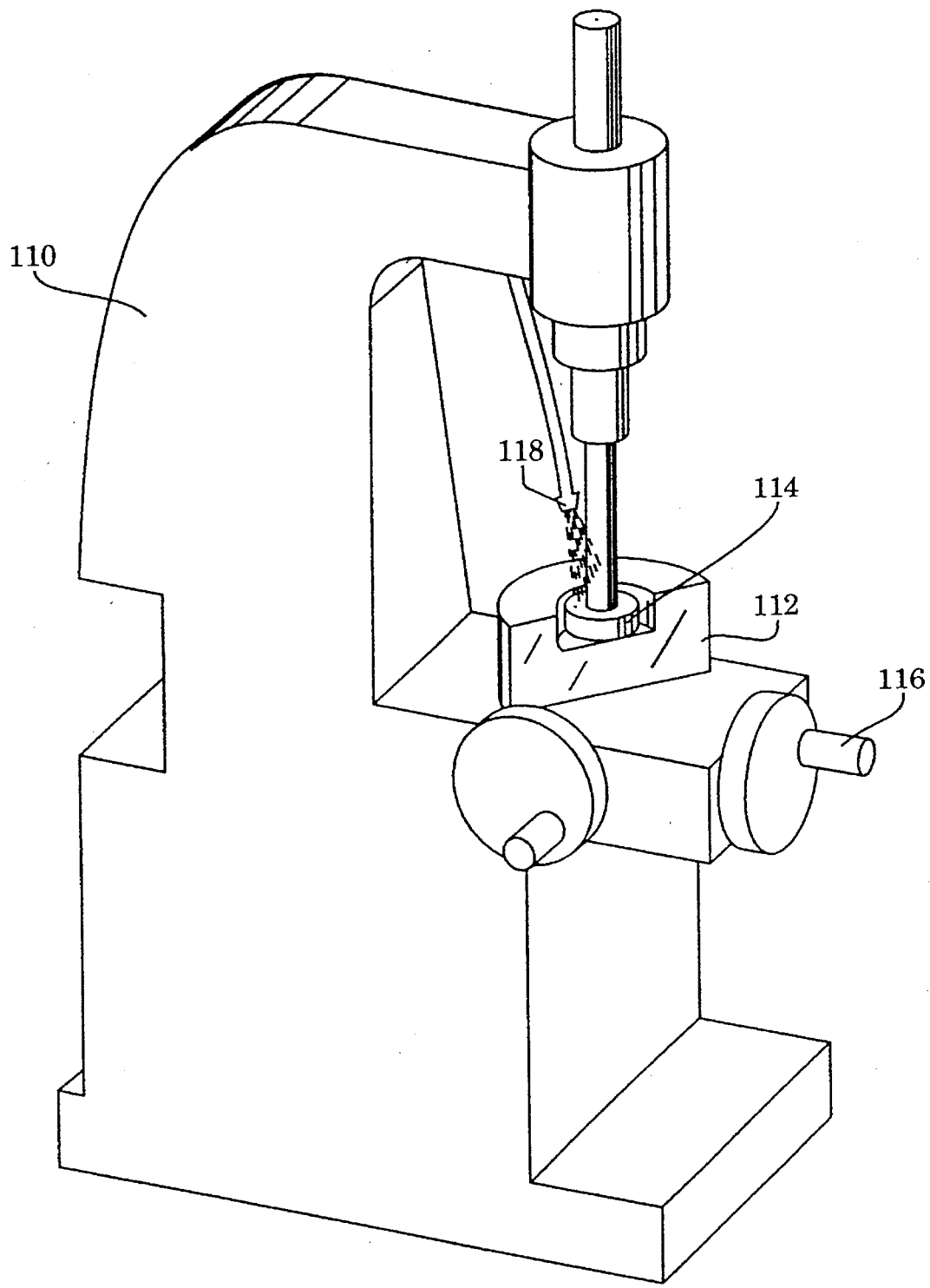
FIG. 1 shows a machining apparatus of the prior art.
Figure 2:
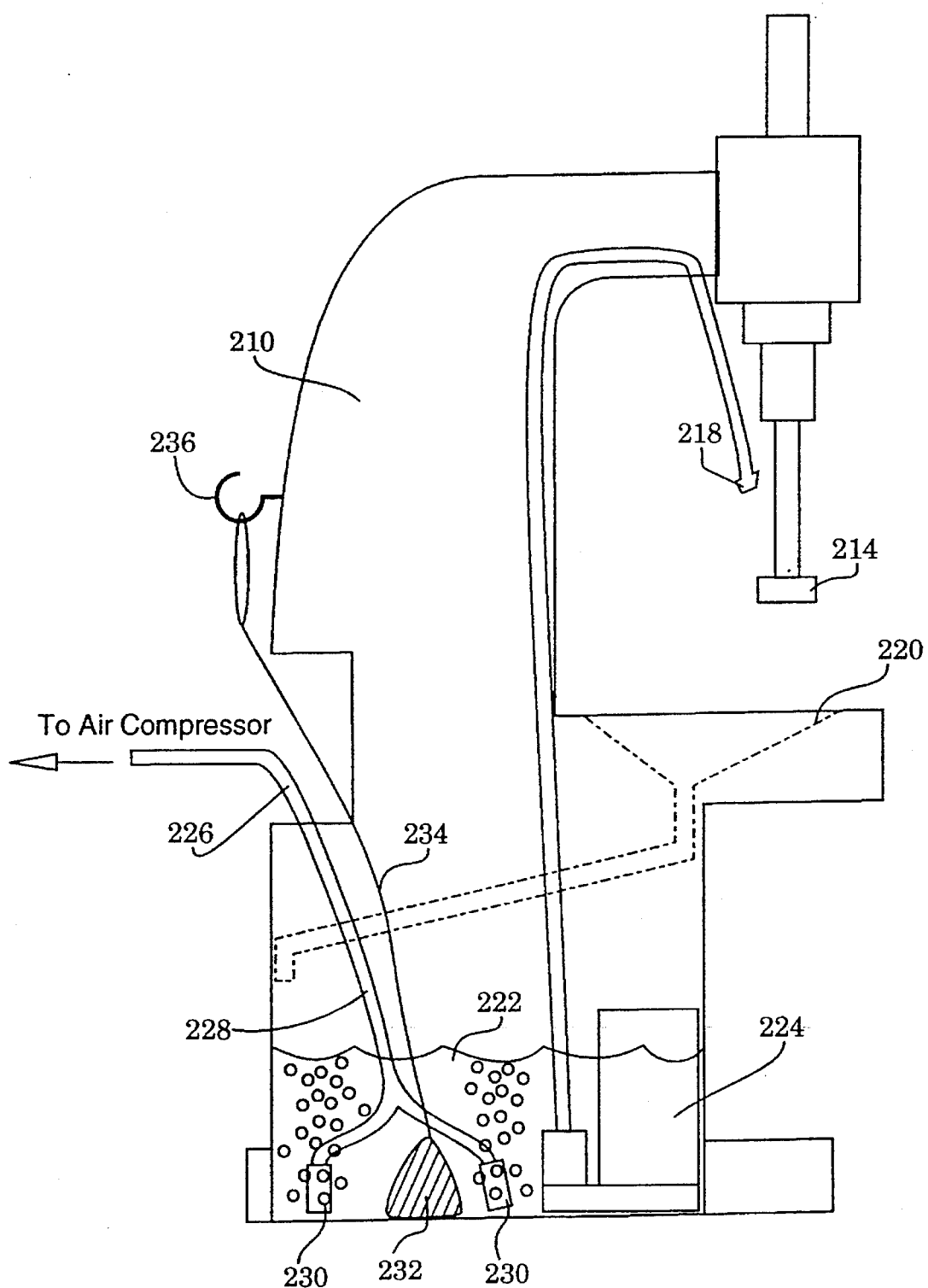
FIG. 2 shows a partial cross-section view of a metal machining apparatus of this invention, including a cutting oil recirculating system, an aeration system, and a source for cultured aerobic bacteria.

FIG. 2 shows a cross-sectional representation of a machining apparatus of this invention. A workpiece (not shown) is supported below a cutting bit 214. During operation of the machining apparatus, the workpiece and the cutting bit 214 are moved relative to one another, as described above. A variety of cutting bits 214 are known to the art, and the specific cutting bit used will vary with the metal being machined and the desired shape of the final product.

Cutting oil is a generic term for that class of oils which are used in metal machining operations. Cutting oil generally comprises one or more mineral oil, chlorinated or sulfurized mineral oil, fatty oil, or mixtures thereof. The cutting oil can also contain anti-corrosion agents, emulsifiers, and the like. It is preferred that the cutting oil used in the subject invention not contain any anti-bacterial agents which would interfere with the proliferation of aerobic bacteria.

Cutting oil is provided at the surface where a metal-shaping bit or blade is used to modify a metal workpiece. Devices which use cutting oil include lathes, cold-saws, milling machines, and the like. Cutting oil provides a lubricating film between the cutting device and the workpiece, thus keeping the cutting area cooled. The continuous flow of cutting oil acts to retain metal shards or flakes formed during the cutting process, and to carry these flakes away from the cutting surface. The cutting oil is removed from the cutting area by a retrieval conduit 220. This retrieval conduit 220 is adapted to deliver used cutting oil from the cutting area to a cutting oil reservoir 222. Within the cutting oil reservoir 222 is a recirculating pump 224 which returns cutting oil to the nozzle 218, continuing the cycle. One or more cutting oil reservoir 222 is generally located within the body of the machining apparatus 210.

In accordance with the invention herein, an aeration system 226 is located at least partially within the cutting oil reservoir 222. The aeration system 226 acts to increase the oxygenation of cutting oil in the cutting oil reservoir. The aeration system 226 is run constantly, whether or not the machining apparatus is being run. Failure of the aeration system 226 can cause die-off of the aerobic bacteria within the system. If the aeration system 226 has been disconnected for 12 hours or more, it is generally recommended that the reservoir 222 system be re-seeded with a new bacteria starter culture 232.

If a standard machining apparatus is to be retro-fitted to include an aeration system, as shown in FIG. 2, an aeration system including an air compressor (not shown) and air tubing 228 is generally used. Air compressors are generally designed to function in a clean, dry environment. Therefore, it is generally convenient to locate the air compressor outside the body of the machining apparatus 210. A variety of appropriate air compressors are known. Care must generally be taken during installation and use of the air compressor to ensure that cutting oil cannot escape the reservoir through or along the air tubing. If possible, the air compressor is placed above the level of the cutting oil in the reservoir to avoid siphoning in the event of power failure. Preferably, an anti-siphon valve is positioned along the air tubing 228.

Air tubing 228 is connected at one end to the air compressor, and at the other end to an air diffuser or airstone. Air tubing 228 is commercially available in varying rigidity, diameters and lengths. Generally, the rigidity, diameter and length of the air tube will be dictated by the specific air compressor used and its proximity to the fluid reservoir.

If flexible air tubing 228 is threaded through curves having a small radius, a rigid pinch protection collar should be provided to avoid crimping of the tubing. In one embodiment, hooks or other such devices are provided to secure the air tubing 228 along its course from the air compressor to the airstone or air diffuser. By securing the air tubing 228 in place, inadvertent crimping of the tubing can be minimized or avoided.

The air tubing 228 is generally connected to one or more air diffusers or airstones 230. When more than one air diffuser or airstone is used, a "T" connector or splitter can be used to provide multiple tubing connections between a single air compressor and multiple airstone units. It is generally preferred that the air diffuser or airstone 230 device be weighted or otherwise secured to remain at or near the bottom of the reservoir.

A wide variety of stone, ceramic, and polymeric airstones 230 are commercially available. Over time, airstones may become clogged. The airstone should be kept clean according to the manufacturer's instructions, and replaced regularly.

Aerobic and anaerobic bacteria are normally present as contaminants in cutting oil. The initiation of aeration will generally start the process of encouraging the proliferation of aerobic bacteria and discouraging the proliferation of anaerobic bacteria. The process of colonization the preferred bacteria can be dramatically shortened by seeding the cutting oil with a starter culture 232 of the desired aerobic bacteria. For best results, this starter culture is introduced into the cutting oil concurrent with, or slightly after, the start of the aeration process.

The temperature of the cutting oil reservoir will generally be about room temperature. Even while cutting oil is being used (and therefore heated) at the cutting surface, the aeration (room temperature air) will act to stabilize the temperature within the reservoir. Generally, however, the temperature should be kept with the range of about 15° C. to about 37° C.

The pH of the cutting oil will generally remain in the range of about 6 to about 8.5.

If the temperature, pH, or other variable causes the bacteria die off and rank odors result, it is recommended that the cutting oil be discarded and fresh cutting oil, with an appropriate bacterial starter culture, be placed into the system.

Generally, the aerobic bacteria which are encouraged for proliferation in the cutting oil aeration system are those bacteria which facilitate an aerobic decomposition of the decomposable organic materials suspended in the cutting oil. Nitrifying bacteria, such as *nitrobacter sp.* and *pseudomonas sp.*, are especially appropriate.

The bacteria starter culture 232 must be compatible with the cutting oil, and must not interfere with the function of the cutting oil. The bacteria starter culture 232 is therefore preferably provided on an inorganic matrix which is insoluble in cutting oil. The inorganic matrix includes cultured aerobic bacteria on surfaces upon and within the matrix. A suitable matrix material is perlite. When a particulate matrix is used, it is generally preferable to contain the particulate material within a flow-through structure. For example, a rigid or flexible plastic outer structure having a plurality of holes therethrough can enclose a non-woven nylon filter membrane. These materials can be hot-stamped to fuse them into a suitable container for a particulate perlite matrix.

In an alternate embodiment (not shown), an oil-based culture medium (including the starter culture) can be provided. In a less preferred embodiment, the starter culture is provided in an aqueous base.

Aerobic bacteria can be cultured from native bacteria in soil, or can be cultured from an aerobic cutting oil environment. Alternatively, a commercially prepared bacterial starter can be used. A variety of suitable aerobic bacteria cultures are commercially available. The "Bio 520" starter culture, available from Harvey Universal, Inc. (Torrance, Calif.) is especially suitable. "Hi-Clean Σ" from Sankai Chemical Co. (Tokyo, Japan) can also be used.

Preferably when a solid matrix starter culture 232 is used, it is weighted to remain at the bottom of the reservoir 222 while permitting easy circulation of the aerated cutting oil. When a solid matrix is used to provide the starter culture, it can be attached to a string or other handling means for ease of retrieval from the reservoir 222. In the pictured embodiment, a string 234 is connected to a hook 236 to provide easy access to the starer culture.

Figure 3:
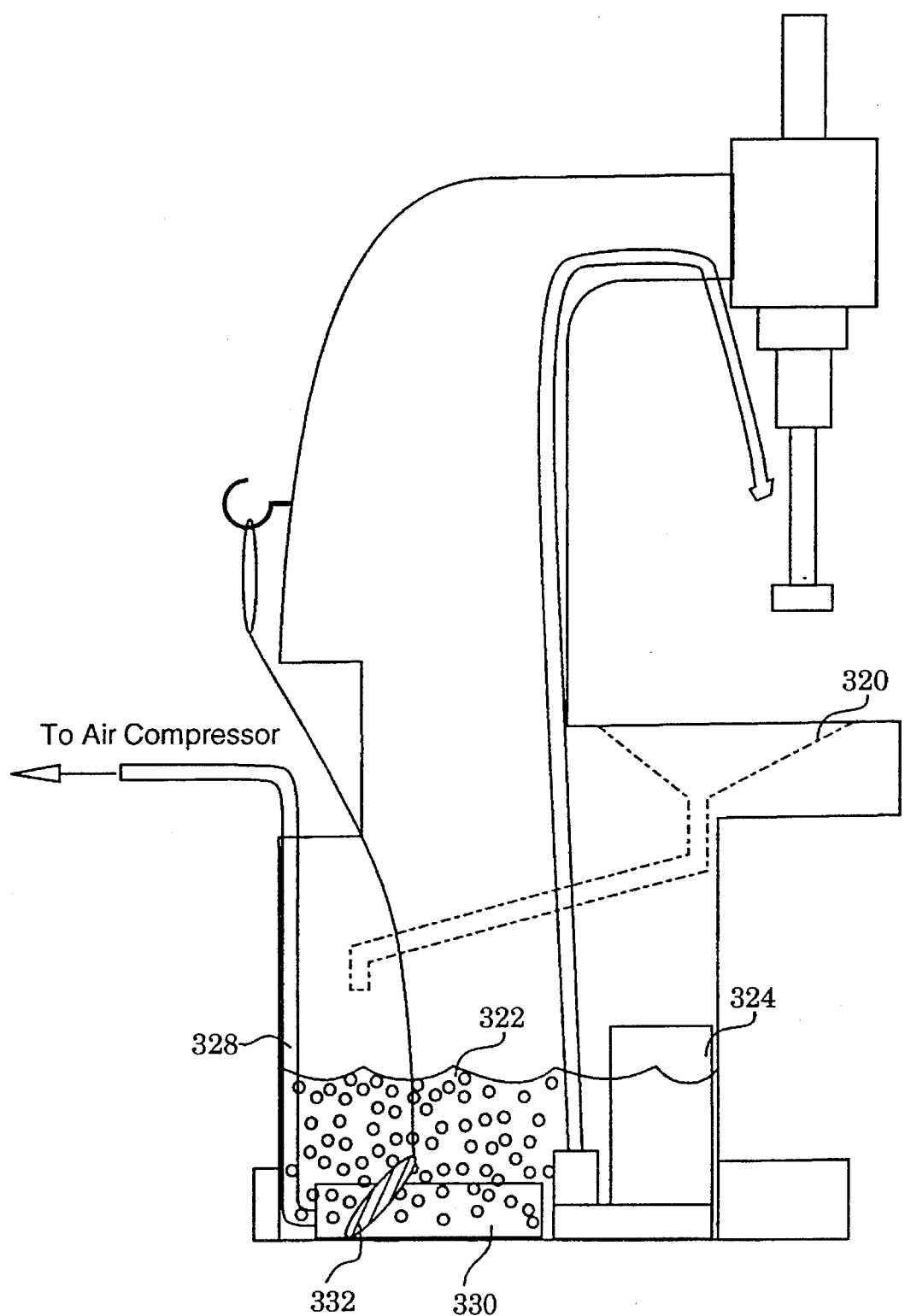
FIG. 3 shows an alternate partial cross-section view of a metal machining apparatus of this invention.

FIG. 3 shows an embodiment in which a single airstone 330 provides aeration for the reservoir 322. Rigid air tubing 328 connects the single airstone 330 to the air compressor (not shown). As pictured, the retrieval conduit 320 preferably provides returning cutting oil at a point distant from the recirculating pump 324. This helps maintain a good circulatory flow, in which cutting oil is brought across the airstone 330 and the starter culture 332.

While the invention has been described in connection with several exemplary embodiments, it will be understood that many modifications will be apparent to those of ordinary skill in the art in light of the above disclosure. Such modifications may include using substitute materials, smaller or greater dimensions, varying the number and placement of starter culture media, using a variety of different aeration devices, and so forth, to achieve substantially the same results in substantially the same way. Reference to the following claims should be made to determine the scope of the invention.

I claim:

1. An improved apparatus for machining metal, said apparatus comprising:

(a) cutting oil delivery nozzle, said nozzle being adapted to provide cutting oil to a cutting area;

(b) a cutting area including a bit for machining metal;

(c) a cutting oil retrieval means to remove used cutting oil from the cutting area and return it to a cutting oil reservoir;

(d) a cutting oil reservoir;

(e) an aeration means located within the cutting oil reservoir, said aeration means acting to increase the oxygenation of cutting oil in the cutting oil reservoir; and (e) a cultured nitrifying bacteria source located in said cutting oil reservoir.

2. An apparatus of claim 1 wherein the bacteria source includes at least one selected from the group consisting of cultured *nitrobacter sp., pseudomonas sp.,* and mixtures thereof.

3. An apparatus of claim 1 wherein the bacteria source further comprises an inorganic base material containing said cultured bacteria supported thereupon.

4. An apparatus of claim 1 wherein the bacteria source further comprises cultured bacteria in an oil base.

5. An apparatus of claim 1 wherein the aeration means comprises at least one from the group consisting of an air diffuser and an airstone.

6. An apparatus of claim 1 wherein said cultured bacteria source comprises an inorganic matrix supporting cultured aerobic bacteria, said matrix being contained within a structure which permits the flow of cutting oil therethrough.

7. An apparatus of claim 6 wherein said flow-through bacteria support structure is removably attached to said apparatus for machining metal.

8. An apparatus of claim 6 wherein said flow-through bacteria support structure is weighted to remain at the bottom of said cutting oil reservoir.

* * * * *